US012295920B2

(12) United States Patent
Fuwa et al.

(10) Patent No.: US 12,295,920 B2
(45) Date of Patent: May 13, 2025

(54) COMPOSITION FOR TREATMENT, PREVENTION, OR AMELIORATION OF ALZHEIMER'S DISEASE, A COMPOSITION FOR SUPPRESSION OF BRAIN NERVE CELL DEATH, A COMPOSITION FOR SUPPRESSION OF MICROGLIA ACTIVATION INDUCED BY AMYLOID β PEPTIDE, AND A COMPOSITION FOR SUPPRESSION OF PGE2, TNF-α, OR IL-1β PRODUCTION INDUCED BY AMYLOID βPEPTIDE

(71) Applicant: House Wellness Foods Corporation, Hyogo (JP)

(72) Inventors: Arisa Fuwa, Itami (JP); Ryusei Uchio, Itami (JP); Kengo Kawasaki, Itami (JP); Koutarou Muroyama, Itami (JP); Shinji Murosaki, Itami (JP)

(73) Assignee: HOUSE WELLNESS FOODS CORPORATION, Hyogo (JP)

( * ) Notice: Subject to any disclaimer, the term of this patent is extended or adjusted under 35 U.S.C. 154(b) by 1107 days.

(21) Appl. No.: 17/253,906

(22) PCT Filed: Jun. 25, 2019

(86) PCT No.: PCT/JP2019/025049
§ 371 (c)(1),
(2) Date: Dec. 18, 2020

(87) PCT Pub. No.: WO2020/004357
PCT Pub. Date: Jan. 2, 2020

(65) Prior Publication Data
US 2021/0267914 A1    Sep. 2, 2021

(30) Foreign Application Priority Data
Jun. 29, 2018  (JP) ................... 2018-124502

(51) Int. Cl.
*A61K 31/12* (2006.01)
*A61P 25/28* (2006.01)

(52) U.S. Cl.
CPC .............. *A61K 31/12* (2013.01); *A61P 25/28* (2018.01)

(58) Field of Classification Search
CPC .............. A61K 36/9066; A61K 31/12; A61K 2236/00; A61K 31/122; A61K 10/30; A61P 37/06; A61P 43/00; A61P 9/00; A23L 33/105; A23L 2/52; A23V 2002/00
See application file for complete search history.

(56) References Cited

FOREIGN PATENT DOCUMENTS

| CN | 1615144 A | 5/2005 |
| JP | 2005-516930 A | 6/2005 |
| JP | 2009-530305 A | 8/2009 |
| JP | 2014-518241 A | 7/2014 |
| TW | 202003435 A | 1/2020 |
| WO | 03/051380 A2 | 6/2003 |
| WO | 2007/109210 A2 | 9/2007 |
| WO | 2013/004740 A1 | 1/2013 |

OTHER PUBLICATIONS

Kitahar et al. Biosci. Biotech. Biochem. 1993, 57, 1137-1140 (Year: 1993).*
Tian et al. (Jul. 19, 2017-Aug. 20, 2021). A Retrospective Study to Investigate the Additive Effectiveness of Chinese Herbal Medicine in Alzheimer's Disease. Identifier NCT03221894 <https://clinicaltrials.gov/ct2/show/NCT03221894> (Year: 2017).*
Cai et al. Microglia, neuroinflammation, and beta-amyloid protein in Alzheimer's disease. Int. J. Neurosci. 2014, 124, 307-321. (Year: 2014).*
Xu et al. Absolute Configurations and NO Inhibitory Activities of Terpenoids from Curcuma longa. J. Agric. Food Chem. 2015, 63, 5805-5812 (Year: 2015).*
Hishikawa et al. Effects of turmeric on Alzheimer's disease with behavioral and psychological symptoms of dementia. Int. J. Ayurveda Res. 2012, 33, 499-504 (Year: 2012).*
Shytle et al. Optimized Turmeric Extract Reduces β-Amyloid and Phosphorylated Tau Protein Burden in Alzheimer's Transgenic Mice. Curr. Alz. Res. Sep. 2012, 500-506 (Year: 2012).*
Kawasaki et al. Biosci. Biotech. Biochem. 2018, 82, 2109-2117 (Year: 2018).*
Zeng et al. Chem. Pharm. Bull. 2007, 55, 940-943 (Year: 2007).*
Sharma et al. (2022). Bioactive Compounds in Turmeric. In Wani, S. A., Singh, A., and Kumar, P. (Eds.), Spice Bioactive Compounds: Properties, Applications, and Health Benefits (pp. 71-91). (Year: 2022).*
Zeng et al., "Chemical constituents of Curcuma longa I: bisabolane sesquiterpenes," Chinese Journal of Medicinal Chemistry, 17(4): 238-241, 262 (2007) (with partial translation).
"Health Care Job Reports—Dementia (especially Alzheimer-type dementia)," Center for Research and Development Strategy of the Organization for Science and Technology Promotion (2002) (see partial English translation).

(Continued)

*Primary Examiner* — Amanda L. Aguirre
(74) *Attorney, Agent, or Firm* — Morgan, Lewis & Bockius LLP (57) ABSTRACT

This invention provides a composition comprising, as an active ingredient, a turmeric-derived ingredient, which is useful for treatment, prevention, or amelioration of Alzheimer's disease. This invention relates to a composition for treatment of Alzheimer's disease, a composition for suppression of brain nerve cell death, a composition for suppression of microglia activation induced by amyloid β peptide, or a composition for suppression of PGE2, TNF-α, or IL-1β production induced by amyloid β peptide comprising, as an active ingredient, a turmeric extract extracted with at least one extraction solvent selected from water and a hydrophilic organic solvent or at least one of termeronol A and termeronol B.

19 Claims, 5 Drawing Sheets

(56) References Cited

OTHER PUBLICATIONS

Ono, "The development of agents for the preventives and therapeutics of Alzheimer's disease based on oligomer hypothesis for developing drugs for the prevention and treatment of Alzheimer's disease based on the oligomeric hypothesis," Bulletin of the Japanese Neurochemical Society, 55 (3): 42-51 (2016).
Mizushima et al., "Of chronic inflammation in Alzheimer's disease: Role and drug discovery," Experimental Medicine, 29 (10) (extra edition): 169(1647)-173(1651) (2011).
Suzumura, "Microglia in neurodegenerative disorders and neuroinflammation," Clinical Neurology 54 (12): 1119-1121 (2014).
Hara, "Molecular Mechanism of Neuroprotective Drugs against Oxidative Stress-Induced Neuronal Cell Death," The Pharmaceutical Society of Japan, 127 (8): 1199-1205 (2007).
Reddy et al., "Amyloid precursor protein-mediated free radicals and oxidative damage: Implications for the development and progression of Alzheimer's disease," Journal of Neurochemistry, 96: 1-13 (2006).
Koo et al., "A water extract of Curcuma longa L. (Zingiberaceae) rescues PC12 cell death caused by pyrogallol or hypoxia/reoxygenation and attenuates hydrogen peroxide induced injury in PC12 cells," Life Sciences, 75 (19): 2363-2375 (2004).
Zeng et al., "New Sesquiterpenes and Calebin Derivatives from Curcuma longa," Chemical & Pharmaceutical Bulletin, 55 (6): 940-943 (2007).
Tohda et al., "Curcumin, a curry spice ingredient, protects against Alzheimer's dementia," Farumashia, 38 (9): 891-892 (2002).
Morishita et al., "Comparison of the content and antioxidant capacity of curcumin from tumeric grown in Kanto," Japanese Journal of Crop Science, 82 (1): 56-62 (2013).
Reddy et al., "Protective effects of a natural product, curcumin, against amyloid beta induced mitochondrial and synaptic toxicities in Alzheimer's disease," Journal of Investigative Medicine, 64 (8): 1220-1234 (2016).
Giri et al., "Curcumin, the active constituent of turmeric, inhibits amyloid peptide-induced cytochemokine gene expression and CCR5-mediated chemotaxis of THP-1 monocytes by modulating early growth response-1 transcription factor," Journal of Neurochemistry, 91 (5): 1199-1210 (2004).
International Search Report issued in corresponding International Patent Application No. PCT/JP2019/025049 dated Sep. 10, 2019.
Yaoxin et al., "Effect of turmeric extract on acetylcholinesterase activity in brain tissue of mice with vascular dementia," Lishizhen Medicine and Materia Medica Research, 22 (7): 1635-1636 (2011).

\* cited by examiner

COMPOSITION FOR TREATMENT, PREVENTION, OR AMELIORATION OF ALZHEIMER'S DISEASE, A COMPOSITION FOR SUPPRESSION OF BRAIN NERVE CELL DEATH, A COMPOSITION FOR SUPPRESSION OF MICROGLIA ACTIVATION INDUCED BY AMYLOID β PEPTIDE, AND A COMPOSITION FOR SUPPRESSION OF PGE2, TNF-α, OR IL-1β PRODUCTION INDUCED BY AMYLOID βPEPTIDE

TECHNICAL FIELD

The present invention relates to a composition for treatment, prevention, or amelioration of Alzheimer's disease, a composition for suppression of brain nerve cell death, a composition for suppression of microglia activation induced by amyloid β peptide, or a composition for suppression of PGE2, TNF-α, or IL-1β production induced by amyloid peptide.

BACKGROUND ART

Alzheimer's disease is a major disease that accounts for 50% to 75% of dementia.

In the brain of a patient with Alzheimer's disease, a senile plaque mainly composed of amyloid β peptide, a neurofibrillary tangle mainly composed of Tau protein, nerve cell death, and the like are observed. While various symptoms including reduced cognitive functions are developed because of Alzheimer's disease, the pathogenic mechanism remains unknown, and there are many problems to be overcome for treatment or prevention of Alzheimer's disease (Non-Patent Literature 1).

Accumulation of a causative substance of Alzheimer's disease; i.e., amyloid peptide, not only induces neuronal cell death but also activates a macrophage cell; i.e., microglia, so that Alzheimer's disease progresses.

When microglia are activated, prostaglandin E2 (PGE2) is produced. PGE2 acts on neuronal cells, exerts excitotoxicity, and induces nerve cell death (Non-Patent Literature 2). PGE2 is increased in the brain of a patient with Alzheimer's disease, and PGE2 further increases the amount of amyloid β peptide (Non-Patent Literature 3). Accordingly, suppression of PGE2 production by microglia is considered effective to suppress the progress of Alzheimer's disease.

When microglia are activated, the tumor necrosis factor α (TNF-α) and interleukin-1β (IL-n) are produced. TNF-α acts on neuronal cells to activate the intracellular signal transmission pathway that induces cell death or to accelerate nerve cell death induced by amyloid β peptide. Accordingly, suppression of TNF-α and IL-β production by microglia is considered effective to suppress the progress of Alzheimer's disease. Non-Patent Literature 4 discloses that microglia activated in the presence of amyloid β peptide releases a humoral factor such as TNF-α and the humoral factor induces neuronal cell death.

In addition, the development and the progress of Alzheimer's disease are considered to be significantly associated with oxidative stress. A possible mechanism thereof is a pathway through which amyloid β peptides released in neuronal cells are accumulated in mitochondria and oxidative stress is induced, which leads to cell death (Non-Patent Literatures 5 and 6).

On the other hand, it has been known that a turmeric comprises a large number of physiologically active substances.

For example, Patent Literature 1 discloses that turmeric-derived oil contains a plurality of bisabolane sesquiterpenoids and it can be used as an anticonvulsant in central nervous system injuries except for Alzheimer's disease (e.g., epilepsy).

Patent Literature 2 discloses that a curcuminoid-containing turmeric extract extracted with supercritical carbon dioxide is administered to a subject suffering from the aggregation or fibrillation of amyloid plaques, in particular, to a subject suffering from Alzheimer's disease.

Patent Literature 3 discloses that fat-soluble rhizome and leaf extracts of turmeric plants are effective for treatment of neurological cerebrovascular accidents. According to Patent Literature 3, neurological cerebrovascular accidents include Alzheimer's disease.

CITATION LIST

Patent Literature

Patent Literature 1: JP 2014-518241 A
Patent Literature 2: JP 2009-530305 A
Patent Literature 3: JP 2005-516930 A

Non Patent Literature

Non Patent Literature 1: Iryo no Fukan Houkokusho (Overall Report on Medicine): Dementia (in particular, Alzheimer-type dementia), March, 2010, (https://www.jst.gojp/crds/report/report05/CRDS-FY2009-WR-09.html)
Non Patent Literature 2: Bulletin of the Japanese Neurochemical Society, Vol. 55 (No. 3), 2016, pp. 42-51
Non Patent Literature 3: Experimental Medicine, Vol. 29 No. 10 (extra edition), 2011, 169 (1647)-173 (1651)
Non Patent Literature 4: Clin. Neurol., 2014; 54: 1119-1121
Non Patent Literature 5: YAKUGAKU ZASSHI 127 (8), 1199-1205, 2007
Non Patent Literature 6: Journal of Neurochemistry, 2006, 96, 1-13

SUMMARY OF INVENTION

Technical Problem

The present invention provides a composition comprising, as an active ingredient, a turmeric-derived ingredient for use in treatment, prevention, or amelioration of Alzheimer's disease, suppression of brain nerve cell death, suppression of microglia activation induced by amyloid β peptide, or suppression of PGE2, TNF-α, or IL-1β production induced by amyloid β peptide.

Solution to Problem

The present inventors have found the following. That is, production of PGE2, TNF-α, or IL-1β is accelerated when macrophage cells are cultured in the presence of aggregates of amyloid β peptides; however, production of PGE2, TNF-α, or IL-1β is suppressed when macrophage cells treated with a water-soluble turmeric extract or termeronol A and termeronol B contained in the extract are cultured in the presence of aggregates of amyloid β peptides. In addition, they found that a water-soluble turmeric extract or termeronol B have activity of suppressing induction of cell death of human neuroblastoma SHSY5Y cells, which are brain nerve cell models, in the supernatant of macrophage cells cultured in the presence of amyloid β peptide and that a water-soluble turmeric extract has activity of suppressing SHSY5Y cell death induced by oxidative stress. This has led to the completion of the present invention described below.

(1) A composition for treatment, prevention, or amelioration of Alzheimer's disease comprising, as an active ingredient, a turmeric extract extracted with at least one extraction solvent selected from water and a hydrophilic organic solvent.

(2) A composition for treatment, prevention, or amelioration of Alzheimer's disease comprising, as an active ingredient, at least one of termeronol A and termeronol B.

(3) The composition according to (2), comprising, as an active ingredient, a turmeric extract extracted with at least one extraction solvent selected from water and a hydrophilic organic solvent, the turmeric extract comprising the at least one of termeronol A and termeronol B.

(4) A composition for suppression of brain nerve cell death comprising, as an active ingredient, a turmeric extract extracted with at least one extraction solvent selected from water and a hydrophilic organic solvent.

(5) A composition for suppression of brain nerve cell death comprising, as an active ingredient, at least one of termeronol A and termeronol B.

(6) The composition according to (5), comprising, as an active ingredient, a turmeric extract extracted with at least one extraction solvent selected from water and a hydrophilic organic solvent, the turmeric extract comprising the at least one of termeronol A and termeronol B.

(7) A composition for suppression of microglia activation induced by amyloid β peptide comprising, as an active ingredient, a turmeric extract extracted with at least one extraction solvent selected from water and a hydrophilic organic solvent.

(8) A composition for suppression of microglia activation induced by amyloid β peptide comprising, as an active ingredient, at least one of termeronol A and termeronol B.

(9) The composition according to (8), comprising, as an active ingredient, a turmeric extract extracted with at least one extraction solvent selected from water and a hydrophilic organic solvent, the turmeric extract comprising the at least one of termeronol A and termeronol B.

(10) A composition for suppression of PEG2 production induced by amyloid β peptide comprising, as an active ingredient, a turmeric extract extracted with at least one extraction solvent selected from water and a hydrophilic organic solvent.

(11) A composition for suppression of PEG2 production induced by amyloid β peptide comprising, as an active ingredient, at least one of termeronol A and termeronol B.

(12) The composition according to (11), comprising, as an active ingredient, a turmeric extract extracted with at least one extraction solvent selected from water and a hydrophilic organic solvent, the turmeric extract comprising the at least one of termeronol A and termeronol B.

(13) A composition for suppression of TNF-α production induced by amyloid β peptide comprising, as an active ingredient, a turmeric extract extracted with at least one extraction solvent selected from water and a hydrophilic organic solvent.

(14) A composition for suppression of TNF-α production induced by amyloid β peptide comprising, as an active ingredient, at least one of termeronol A and termeronol B.

(15) The composition according to (14), comprising, as an active ingredient, a turmeric extract extracted with at least one extraction solvent selected from water and a hydrophilic organic solvent, the turmeric extract comprising the at least one of termeronol A and termeronol B.

(16) A composition for suppression of IL-1β production induced by amyloid β peptide comprising, as an active ingredient, a turmeric extract extracted with at least one extraction solvent selected from water and a hydrophilic organic solvent.

(17) A composition for suppression of IL-1β production induced by amyloid β peptide comprising, as an active ingredient, at least one of termeronol A and termeronol B.

(18) The composition according to (17), comprising, as an active ingredient, a turmeric extract extracted with at least one extraction solvent selected from water and a hydrophilic organic solvent, the turmeric extract comprising the at least one of termeronol A and termeronol B.

(19) The composition according to (7), (8), or (9), wherein the microglia activation induced by amyloid β peptide encompasses production of at least one substance selected from among PGE2, TNF-α, and IL-1β by microglia induced by amyloid β peptide.

(20) A composition for suppression of production of at least one substance selected from among PGE2, TNF-α, and IL-1β induced by amyloid β peptide, the composition comprising, as an active ingredient, a turmeric extract extracted with at least one extraction solvent selected from water and a hydrophilic organic solvent.

(21) A composition for suppression of production of at least one substance selected from among PGE2, TNF-α, and IL-1β induced by amyloid β peptide, the composition comprising, as an active ingredient, at least one of termeronol A and termeronol B.

(22) The composition according to (21), comprising, as an active ingredient, a turmeric extract extracted with at least one extraction solvent selected from water and a hydrophilic organic solvent, the turmeric extract comprising the at least one of termeronol A and termeronol B.

(23) Use of a turmeric extract extracted with at least one extraction solvent selected from water and a hydrophilic organic solvent for production of a composition for treatment, prevention, or amelioration of Alzheimer's disease.

(24) Use of at least one of termeronol A and termeronol B for production of a composition for treatment, prevention, or amelioration of Alzheimer's disease.

(25) Use of a turmeric extract extracted with at least one extraction solvent selected from water and a hydrophilic organic solvent for production of a medicament for treatment, prevention, or amelioration of Alzheimer's disease.

(26) Use of at least one of termeronol A and termeronol B for production of a medicament for treatment, prevention, or amelioration of Alzheimer's disease.

(27) A method for treatment, prevention, or amelioration of Alzheimer's disease comprising:
administrating a turmeric extract extracted with at least one extraction solvent selected from water and a hydrophilic organic solvent to a subject in need of treatment, prevention, or amelioration of Alzheimer's disease; and
treating, preventing, or ameliorating Alzheimer's disease in the subject.

(28) A method for treatment, prevention, or amelioration of Alzheimer's disease comprising:
administrating at least one of termeronol A and termeronol B to a subject in need of treatment, prevention, or amelioration of Alzheimer's disease; and
treating, preventing, or ameliorating Alzheimer's disease in the subject.

(29) A turmeric extract extracted with at least one extraction solvent selected from water and a hydrophilic organic solvent for use in treatment, prevention, or amelioration of Alzheimer's disease of a subject in need of treatment, prevention, or amelioration of Alzheimer's disease.

(30) At least one of termeronol A and termeronol B for use in treatment, prevention, or amelioration of Alzheimer's disease of a subject in need of treatment, prevention, or amelioration of Alzheimer's disease.

(31) The use according to (24), the use according to (26), the method according to (28), or the at least one of termeronol A and termeronol B according to (30), wherein the at least one of termeronol A and termeronol B is in the form of a turmeric extract extracted with at least one extraction solvent selected from water and a hydrophilic organic solvent.

(32) Use of a turmeric extract extracted with at least one extraction solvent selected from water and a hydrophilic organic solvent for production of a composition for suppression of brain nerve cell death.

(33) Use of at least one of termeronol A and termeronol B for production of a composition for suppression of brain nerve cell death.

(34) Use of a turmeric extract extracted with at least one extraction solvent selected from water and a hydrophilic organic solvent for production of a medicament for suppression of brain nerve cell death.

(35) Use of at least one of termeronol A and termeronol B for production of a medicament for suppression of brain nerve cell death.

(36) A method for suppression of brain neuronal cell death in vivo or in vitro comprising:
administrating a turmeric extract extracted with at least one extraction solvent selected from water and a hydrophilic organic solvent to brain neuronal cells in vivo or in vitro; and
suppressing cell death of the brain neuronal cells.

(37) A method for suppression of brain neuronal cell death in vivo or in vitro comprising:
administrating at least one of termeronol A and termeronol B to brain neuronal cells in vivo or in vitro; and
suppressing cell death of the brain neuronal cells.

(38) A turmeric extract extracted with at least one extraction solvent selected from water and a hydrophilic organic solvent for use in suppression of brain neuronal cell death in vivo or in vitro.

(39) At least one of termeronol A and termeronol B for use in suppression of brain neuronal cell death in vivo or in vitro.

(40) The use according to (33), the use according to (35), the method according to (37), or the at least one of termeronol A and termeronol B according to (39), wherein the at least one of termeronol A and termeronol B is in the form of a turmeric extract extracted with at least one extraction solvent selected from water and a hydrophilic organic solvent.

(41) Use of a turmeric extract extracted with at least one extraction solvent selected from water and a hydrophilic organic solvent for production of a composition for suppression of microglia activation induced by amyloid $\beta$ peptide.

(42) Use of at least one of termeronol A and termeronol B for production of a composition for suppression of microglia activation induced by amyloid $\beta$ peptide.

(43) Use of a turmeric extract extracted with at least one extraction solvent selected from water and a hydrophilic organic solvent for production of a medicament for suppression of microglia activation induced by amyloid $\beta$ peptide.

(44) Use of at least one of termeronol A and termeronol B for production of a medicament for suppression of microglia activation induced by amyloid $\beta$ peptide.

(45) A method for suppression of microglia activation induced by amyloid $\beta$ peptide in vivo or in vitro comprising:
administrating a turmeric extract extracted with at least one extraction solvent selected from water and a hydrophilic organic solvent to microglia in vivo or in vitro; and
suppressing activation of the microglia induced by amyloid $\beta$ peptide.

(46) A method for suppression of microglia activation induced by amyloid $\beta$ peptide in vivo or in vitro comprising:
administrating at least one of termeronol A and termeronol B to microglia in vivo or in vitro; and
suppressing activation of the microglia induced by amyloid $\beta$ peptide.

(47) A turmeric extract extracted with at least one extraction solvent selected from water and a hydrophilic organic solvent for use in suppression of microglia activation induced by amyloid $\beta$ peptide in vivo or in vitro.

(48) At least one of termeronol A and termeronol B for use in suppression of microglia activation induced by amyloid $\beta$ peptide in vivo or in vitro.

(49) The use according to (42), the use according to (44), the method according to (46), or the at least one of termeronol A and termeronol B according to (48), wherein the at least one of termeronol A and termeronol B is in the form of a turmeric extract extracted with at least one extraction solvent selected from water and a hydrophilic organic solvent.

(50) The use according to (41), (42), or (49), the use according to (43), (44), or (49), the method according to (45), (46), or (49), or the at least one of termeronol A and termeronol B according to (47), (48), or (49), wherein the microglia activation induced by amyloid $\beta$ peptide encompasses production of at least one substance selected from among PGE2, TNF-$\alpha$, and IL-1$\beta$ by microglia induced by amyloid $\beta$ peptide.

(51) Use of a turmeric extract extracted with at least one extraction solvent selected from water and a hydrophilic organic solvent for production of a composition for suppression of production of at least one substance selected from among PGE2, TNF-α, and IL-1β induced by amyloid β peptide.
(52) Use of at least one of termeronol A and termeronol B for production of a composition for suppression of production of at least one substance selected from among PGE2, TNF-α, and IL-1β induced by amyloid β peptide.
(53) Use of a turmeric extract extracted with at least one extraction solvent selected from water and a hydrophilic organic solvent for production of a composition for suppression of production of at least one substance selected from among PGE2, TNF-α, and IL-1β induced by amyloid β peptide.
(54) Use of at least one of termeronol A and termeronol B for production of a composition for suppression of production of at least one substance selected from among PGE2, TNF-α, and IL-1β induced by amyloid β peptide.
(55) A method for suppressing production of at least one substance selected from among PGE2, TNF-α, and IL-1β induced by amyloid β peptide comprising:
administrating a turmeric extract extracted with at least one extraction solvent selected from water and a hydrophilic organic solvent to a subject in need of suppression of production of at least one substance selected from among PGE2, TNF-α, and IL-1β induced by amyloid β peptide; and
suppressing production of at least one substance selected from among PGE2, TNF-α, and IL-1f3 induced by amyloid β peptide in the subject.
(56) A method for suppressing production of at least one substance selected from among PGE2, TNF-α, and IL-1β induced by amyloid β peptide comprising:
administrating at least one of termeronol A and termeronol B to a subject in need of suppression of production of at least one substance selected from among PGE2, TNF-α, and IL-1β induced by amyloid β peptide; and
suppressing production of at least one substance selected from among PGE2, TNF-α, and IL-1f3 induced by amyloid β peptide in the subject.
(57) A turmeric extract extracted with at least one extraction solvent selected from water and a hydrophilic organic solvent for use in suppression of production of at least one substance selected from among PGE2, TNF-α, and IL-1β induced by amyloid β peptide to a subject in need of suppression of production of at least one substance selected from among PGE2, TNF-α, and IL-1β induced by amyloid β peptide.
(58) At least one of termeronol A and termeronol B for use in suppression of production of at least one substance selected from among PGE2, TNF-α, and IL-1β induced by amyloid β peptide in a subject in need of suppression of production of at least one substance selected from among PGE2, TNF-α, and IL-1β induced by amyloid β peptide.
(59) The use according to (52), the use according to (54), the method according to (56), or the at least one of termeronol A and termeronol B according to (58), wherein the at least one of termeronol A and termeronol B is in the form of a turmeric extract extracted with at least one extraction solvent selected from water and a hydrophilic organic solvent.

This description contains part or all of the content as disclosed in the description and/or drawings of Japanese Patent Application No. 2018-124502, based on which the present application claims a priority.

Advantageous Effects of Invention

The present invention provides a composition for treatment, prevention, or amelioration of Alzheimer's disease, suppression of brain nerve cell death, suppression of microglia activation induced by amyloid β peptide, or suppression of production of PGE2, TNF-α, or IL-1β induced by amyloid β peptide, the composition comprising, as an active ingredient, a turmeric extract extracted with at least one extraction solvent selected from water and a hydrophilic organic solvent or at least one of termeronol A and termeronol B.

DESCRIPTION OF EMBODIMENTS

<Turmeric Extract>

In the present invention, the term "turmeric extract" refers to an extract of a plant material derived from a plant of the genus *Curcuma* in the family Zingiberaceae obtained with the use of an extraction solvent (i.e., a turmeric extract). A turmeric extract is not limited to a solvent extract obtained via extraction with an extraction solvent. A resultant obtained via fractionation or purification such as column chromatography of the solvent extract is also within the scope of the turmeric extract. A turmeric extract used in the present invention can be in the form of an extract after the completion of an extraction procedure (including a fractionation or purification procedure when performed), a concentrate obtained by partially removing a solvent from the extract, or a dry matter obtained by removing a solvent from the extract. A solvent can be removed from an extract by allowing the solvent to evaporate via, for example, heating and/or depression. Methods of heating and depression are not particularly limited. For example, conventional methods can be employed.

Examples of the plant materials include rhizomes of plants of the genus *Curcuma* in the family Zingiberaceae, such as *Curcuma longa* (turmeric), *Curcuma aromatica, Curcuma zedoaria, Curcuma phaeocaulis, Curcuma kwangsiensis, Curcuma wenyujin*, and *Curcuma xanthorrhiza*. A rhizome of *Curcuma longa* is particularly preferable as the plant material. A rhizome collected from soil may be used. An adequate part of a rhizome may be used in its original form. A part of a rhizome cut into adequate dimensions or configuration may be used. A grounded rhizome may be used. Such plant material may have been dried.

At least one extraction solvent selected from water and a hydrophilic organic solvent can be used. At least one extraction solvent selected from water and a hydrophilic organic solvent may be water, a hydrophilic organic solvent, or a mixed solvent of water and a hydrophilic organic solvent. A hydrophilic organic solvent may be a mixed solvent of a plurality of hydrophilic organic solvents. The "water" includes hot water. As such hot water, for example, hot water with a temperature of 95° C. or higher can be used. The hydrophilic organic solvent may be, for example, at least one type of alcohol (which may also be a mixed solvent consisting of multiple types of alcohols). The alcohol is not particularly limited, and ethanol is preferable. When a mixed solvent of alcohol and water is used as an extraction solvent, the mixing ratio between alcohol and water is not particularly limited. The mixing ratio is preferably in the range of 10:90 to 90:10, and more preferably in the range of 20:80 to 50:50, for example, at a weight ratio.

Also, supercritical carbon dioxide can be used as an extraction solvent.

A method for obtaining a turmeric extract from a plant material is not particularly limited.

In the present invention, the turmeric extract is preferably a turmeric extract with the extraction solvent described above containing termeronol A and termeronol B.

Termeronol A and termeronol B are each a compound having a planar structure shown below.

[Formula 1]

Termeronol A

[Formula 2]

Termeronol B

<Termeronol a and Termeronol B>

At least one of termeronol A and termeronol B used in the present invention (hereafter, it may be referred to as an "active compound," according to need) may be derived from a plant or it may be artificially synthesized. For example, optically active (+)-termeronol A can be synthesized in accordance with the method described in Biosci. Biotechnol. Biochem., 1993; 57 (7): 1137-40.

In a naturally-occurring substance separated from a turmeric extract, termeronol A and termeronol B are each known to comprise an S configuration at the carbon at position 6 in the partial structure of 2-methyl-2-hepten-4-one. In the present invention, however, it is sufficient if termeronol A and termeronol B each have the planar structure described above, and it may be an S configuration, an R configuration, or a mixture of S and R configurations.

The active compound used in the present invention is more preferably derived from a plant material, and further preferably derived from a plant of the genus *Curcuma* in the family Zingiberaceae. Specific examples of a plant of the genus *Curcuma* in the family Zingiberaceae and parts thereof are as described above. An active compound can be obtained from a part, such as a rhizome, of a plant of the genus *Curcuma* in the family Zingiberaceae.

An active compound can be extracted from a plant material containing the same. A method of extraction is as described above. An active compound may be in the form of a plant extract and, in particular, a turmeric extract extracted with at least one extraction solvent selected from water and a hydrophilic organic solvent.

Alternatively, a fraction of a highly-purified active compound prepared from a plant extract containing an active compound may be used in the present invention, and such fraction may be integrated into the composition of the present invention. For example, a plant extract containing an active compound may be subjected to liquid-liquid distribution using ethyl acetate/water, and a highly purified active compound can be obtained in an ethyl acetate fraction. Alternatively, a plant extract containing an active compound or a fraction thereof may be subjected to purification via chromatography to obtain a highly-purified active compound. Examples of chromatography techniques that can be employed include reversed-phase column chromatography and normal-phase thin-layer chromatography.

A plant extract containing an active compound or a fraction thereof may be subjected to processing, such as dehydration, pulverization, granulation, or fluidization, in accordance with a conventional technique.

<The Composition of the Present Invention>

An aspect of the present invention relates to a composition for treatment, prevention, or amelioration of Alzheimer's disease comprising, as an active ingredient, the turmeric extract or the at least one of termeronol A and termeronol B. Administration of the composition according to this aspect of the present invention to a subject such as a human enables treatment, prevention, or amelioration of Alzheimer's disease in the subject. The active ingredient is administered in an effective amount for treatment, prevention, or amelioration of Alzheimer's disease. A route of administration is preferably oral administration, intranasal administration, intracerebral administration, or intraspinal administration, more preferably oral or intranasal administration, and particularly preferably oral administration. The composition of the present invention suppresses production of PGE2, TNF-α, or IL-1β by microglia activated by amyloid β peptide and induction of nerve cell death associated with such substances in the brain. This enables treatment, prevention, or amelioration of Alzheimer's disease.

Another aspect of the present invention relates to a composition for suppression of microglia activation induced by amyloid β peptide comprising, as an active ingredient, the turmeric extract or the at least one of termeronol A and termeronol B. Administration of the composition according to this aspect of the present invention to a subject such as a human enables suppression of microglia activation induced by amyloid β peptide in the subject. The active ingredient is administered in an effective amount for suppression of microglia activation induced by amyloid β peptide. A route of administration is preferably oral administration, intranasal administration, intracerebral administration, or intraspinal administration, more preferably oral or intranasal administration, and particularly preferably oral administration. In the brain of a patient with Alzheimer's disease, it is deduced that amyloid β peptide activates microglia, the activated microglia produce PGE2, TNF-α, or IL-1β, and brain nerve cell death is induced. With the use of the composition of the present invention, activation of microglia by amyloid β peptide can be suppressed.

Another aspect of the present invention relates to a composition for suppression of brain nerve cell death comprising, as an active ingredient, the turmeric extract or the at least one of termeronol A and termeronol B. The present inventors found that the culture supernatant of macrophage cells cultured in the presence of amyloid β peptide would induce cell death of human neuroblastoma SHSY5Y cells, which are brain nerve cell or central neuronal cell models, while the culture supernatant of macrophage cells treated with the turmeric extract or termeronol B in advance and then cultured in the presence of amyloid peptide would have a weaker activity in inducing cell death of the human neuroblastoma SHSY5Y cells. The present inventors also found that the turmeric extract had activity of suppressing SHSY5Y cell death induced by oxidative stress. Such finding verifies that the turmeric extract or at least one of termeronol A and termeronol B has activity of suppressing cell death of brain neuronal cells or central neuronal cells induced by oxidative stress or suppressing cell death induced by microglia activated by amyloid β peptide. Administration of the composition according to this aspect of the present invention to a subject such as a human enables suppression of cell death of brain neuronal cells or central neuronal cells and, in particular, cell death of brain neuronal cells or central neuronal cells associated with PGE2, TNF-α, or IL-1β produced by microglia activated by amyloid β peptide or cell death of brain neuronal cells or central neuronal cells associated with oxidative stress in the subject. The active ingredient is administered in an effective amount for suppression of brain nerve cell or central nerve cell death. A route of administration is preferably oral administration, intranasal administration, intracerebral administration, or intraspinal administration, more preferably oral or intranasal administration, and particularly preferably oral administration.

Another aspect of the present invention relates to a composition for suppression of production of PGE2, TNF-α, or IL-1β induced by amyloid β peptide, the composition comprising, as an active ingredient, the turmeric extract or the at least one of termeronol A and termeronol B. Administration of the composition according to this aspect of the present invention to a subject such as a human enables suppression of production of PGE2, TNF-α, or IL-1β induced by amyloid β peptide, and, in particular, production of PGE2, TNF-α, or IL-1β by microglia activated by amyloid β peptide in the subject. The active ingredient is administered in an effective amount for suppression of production of PGE2, TNF-α, or IL-1β induced by amyloid β peptide. A route of administration is preferably oral administration, intranasal administration, intracerebral administration, or intraspinal administration, more preferably oral or intranasal administration, and particularly preferably oral administration.

The composition of the present invention may be in the form of, for example, a pharmaceutical product, a food or beverage product, a feed, a food additive, or a feed additive, and it is preferably in the form of a pharmaceutical product or a food or beverage product. Food or beverage products in the form of, for example, foods with functional claims, foods for specified health use (FOSHU), and nutritional supplements are within the scope of the present invention. The composition of the present invention is preferably ingested or administered through the mouth or nose, and it is more preferably ingested or administered through the mouth.

The composition according to a preferable embodiment of the present invention comprises, as an active ingredient, the turmeric extract in a manner such that the composition comprises 80 μg or more termeronol A and 20 μg or more termeronol B per daily ingestion or administration amount of the composition, and preferably per daily ingestion or administration amount of the composition ingested by or administered to one human, in particular, one adult human, per day. Thus, activity of treatment, prevention, or amelioration of Alzheimer's disease, activity of suppression of brain nerve cell death, activity of suppression of microglia activation induced by amyloid β peptide, and activity of suppression of PGE2, TNF-α, or IL-1β production induced by amyloid β peptide can be effectively achieved. Here, the "daily ingestion or administration amount" is typically 0.1 g to 500 g of the composition of the present invention when ingested or administered orally or nasally, and preferably orally. The composition of the present invention may be ingested or administered continuously, or may be ingested or administered when needed.

The composition comprising, as an active ingredient, the turmeric extract according to an embodiment of the present invention may be the turmeric extract per se, or the composition may comprise the turmeric extract and one or more other ingredients. When the composition of the present invention comprises the turmeric extract and one or more other ingredients, the composition may be in the form of a composition of the turmeric extract mixed with one or more other ingredients, a formulation of the turmeric extract integrated with one or more other ingredients formulated by an adequate means, or a composition of the formulation of the turmeric extract integrated with one or more other ingredients further mixed with other ingredients.

The composition according to an embodiment of the present invention comprises, as an active ingredient, at least one of termeronol A and termeronol B in a manner such that the composition comprises 100 μg or more termeronol A and termeronol B in total per daily ingestion or administration amount of the composition, and preferably per daily ingestion or administration amount of the composition ingested by or administered to one human, in particular, one adult human, per day. Also, the composition according to an embodiment of the present invention comprises, as an active ingredient, at least one of termeronol A and termeronol B in a manner such that the composition preferably comprises 80 μg or more termeronol A and/or 20 μg or more termeronol B, and more preferably 80 μg or more termeronol A and 20 μg or more termeronol B per daily ingestion or administration amount of the composition, and preferably per daily dose of the composition ingested by or administered to one human, in particular, one adult human, per day. According to such embodiments, activity of treatment, prevention, or amelioration of Alzheimer's disease, activity of suppression of brain nerve cell death, activity of suppression of microglia activation induced by amyloid β peptide, and activity of suppression of PGE2, TNF-α, or IL-1β production induced by amyloid β peptide can be effectively achieved. Here, the "daily ingestion or administration amount" of the composition is typically 0.1 g to 500 g of the composition of the present invention when ingested or administered orally or nasally, and preferably orally. The composition of the present invention may be continuously ingested or administered, or it may be ingested or administered according to need.

The composition comprising, as an active ingredient, at least one of termeronol A and termeronol B according to an embodiment of the present invention may be a compound of at least one of termeronol A and termeronol B per se, or the composition may comprise the compound and one or more other ingredients. When the composition of the present invention comprises the compound and one or more other ingredients, the composition may be in the form of a composition of the compound mixed with one or more other ingredients, a formulation of the compound integrated with one or more other ingredients formulated by an adequate means, or a composition of the formulation of the compound integrated with one or more other ingredients further mixed with other ingredients.

The form of the composition of the present invention is not particularly limited. For example, it may be a liquid, fluid, gel, semi-solid, or solid form.

The composition of the present invention can comprise one or more types of other ingredients without particular limitation. Preferable examples of such other ingredients include ingredients that are acceptable in the final form, such as a pharmaceutical product, a food or beverage product, a feed, a food additive, or a feed additive, and are orally ingestible.

Examples of other ingredients include sweeteners, acidulants, vitamins, minerals, thickeners, emulsifiers, antioxidants, and water. According to need, pigments, aroma chemicals, preservatives, antiseptic agents, fungicides, other physiologically active substances, or the like may be added.

Examples of sweeteners include: monosaccharides and disaccharides, such as glucose, fructose, sucrose, lactose, maltose, palatinose, trehalose, and xylose; isomerized glucose syrup (e.g., glucose-fructose syrup, fructose-glucose syrup, and an isomerized sugar mixture), sugar alcohols (e.g., erythritol, xylitol, lactitol, Palatinit™, sorbitol, and reduced starch syrup), honey, and high-intensity sweeteners (e.g., sucralose, acesulfame potassium, thaumatin, stevia, and aspartame).

Examples of acidulants include citric acid, malic acid, gluconic acid, tartaric acid, lactic acid, phosphoric acid, and salts thereof. Each of such substances can be used alone or two or more thereof can be used in combination.

Examples of vitamins include vitamin A, vitamin B1, vitamin B2, vitamin B6, vitamin E, niacin, and inositol.

Examples of minerals include calcium, magnesium, zinc, and iron.

Examples of thickeners include carrageenan, gellan gum, xanthan gum, gum Arabic, tamarind gum, guar gum, Locust bean gum, karaya gum, agar, gelatin, pectin, soybean polysaccharides, and carboxymethyl cellulose (CMC).

Examples of emulsifiers include glycerin fatty acid ester, sucrose fatty acid ester, sorbitan fatty acid ester, lecithin, plant sterol, and saponin.

Examples of antioxidants include vitamin C, tocopherol (vitamin E), and enzyme-treated rutin.

The other ingredients can be adequately incorporated in adequate amounts that a person skilled in the art generally employs for food or beverage, pharmaceutical, or other compositions.

The formulation of the compound integrated with one or more other ingredients formulated by an adequate means may be in the form of a solid composition, such as powder, granules, capsules, and tablets (including coated tablets such as sugar-coated tablets, multilayer tablets, orally disintegrating tablets, and chewable tablets), or a liquid composition such as a solution.

<Method for Treatment, Prevention, or Amelioration of Alzheimer's Disease>

Another aspect of the present invention relates to a method for treatment, prevention, or amelioration of Alzheimer's disease comprising:

administrating the turmeric extract or at least one of termeronol A and termeronol B to a subject in need of treatment, prevention, or amelioration of Alzheimer's disease; and treating, preventing, or ameliorating Alzheimer's disease in the subject.

The turmeric extract or at least one of termeronol A and termeronol B used in the method according to the present aspect can be in the form of the composition of the present invention described above.

The subject in the method according to the present aspect is typically a human. The subject may also be non-human mammals.

In the method according to the present aspect, a route of administration is preferably oral administration, intranasal administration, intracerebral administration, or intraspinal administration, more preferably oral or intranasal administration, and particularly preferably oral administration.

In the method according to the present aspect, the amount of the turmeric extract or at least one of termeronol A and termeronol B to be administered to the subject is not particularly limited, provided that it is an effective amount for treatment, prevention, or amelioration of Alzheimer's disease. When the subject is an adult, for example, the amount of the turmeric extract or at least one of termeronol A and termeronol B to be administered to an adult per day is preferably 100 µg or more termeronol A and termeronol B in total, more preferably 80 µg or more termeronol A and/or 20 µg or more termeronol B, and particularly preferably 80 µg or more termeronol A and 20 µg or more termeronol B.

<Method for Suppression of Brain Neuronal Cell Death>

A further aspect of the present invention relates to a method for suppression of brain neuronal cell death in vivo or in vitro comprising:

administrating the turmeric extract or at least one of termeronol A and termeronol B to brain neuronal cells in vivo or in vitro; and suppressing cell death of the brain neuronal cells.

The turmeric extract or at least one of termeronol A and termeronol B used in the method according to the present aspect can be in the form of the composition of the present invention described above.

The brain neuronal cells in the method according to the present aspect is derived typically from a human. The brain neuronal cells may also be derived from non-human mammals, such as rat, mouse, or cow.

The brain neuronal cells may be cell lines derived from brain neuronal cells or central neuronal cells, such as human neuroblastoma SHSY5Y cells.

In the method according to the present aspect, a method of administration of the turmeric extract or at least one of termeronol A and termeronol B to brain neuronal cells in vitro comprises adding the turmeric extract or at least one of termeronol A and termeronol B at adequate concentration to a medium in which the brain neuronal cells are cultured. The concentration of the turmeric extract or at least one of termeronol A and termeronol B to be added to the medium is not particularly limited. When the turmeric extract is administered, the concentration is preferably 10 µg/ml or higher, more preferably 20 µg/ml or higher, and particularly preferably 50 µg/ml or higher to preferably 1,000 µg/ml or lower, and more preferably 500 µg/ml or lower. When at least one of termeronol A and termeronol B is administered, the concentration of termeronol A and termeronol B in total is preferably 1 µM or higher, more preferably 10 µM or higher, particularly preferably 20 µM or higher, and most preferably 50 µM or higher to preferably 1,000 µM or lower, more preferably 500 µM or lower, and particularly preferably 200 µM or lower.

In the method according to the present aspect, a method of administration of the turmeric extract or at least one of termeronol A and termeronol B to brain neuronal cells in vivo is not particularly limited, provided that the turmeric extract or at least one of termeronol A and termeronol B can be delivered to brain neuronal cells in vivo. For example, oral administration, intranasal administration, intracerebral administration, or intraspinal administration is preferable, oral or intranasal administration is more preferable, and oral administration is particularly preferable. When the turmeric extract or at least one of termeronol A and termeronol B is administered to brain neuronal cells in vivo, the amount of administration is not particularly limited, provided that brain neuronal cell death can be effectively suppressed. When it is administered to an adult, for example, the amount of the turmeric extract or at least one of termeronol A and termeronol B to be administered to an adult per day is preferably 100 µg or more termeronol A and termeronol B in total, more preferably 80 µg or more termeronol A and/or 20 µg or more termeronol B, and particularly preferably 80 µg or more termeronol A and 20 µg or more termeronol B.

In the method according to the present aspect, the turmeric extract or at least one of termeronol A and termeronol B is administered to brain neuronal cells in vivo or in vitro, and the turmeric extract or at least one of termeronol A and termeronol B is then kept in contact with the brain neuronal cells for an adequate period of time, such as 5 hours or longer, preferably 12 hours or longer, more preferably 20 hours or longer, and particularly preferably 24 hours or longer to preferably 72 hours or shorter, more preferably 48 hours or shorter, and particularly preferably 36 hours or shorter. Thus, the brain neuronal cell death can be suppressed.

<Method for Suppression of Microglia Activation Induced by Amyloid β Peptide>

A further aspect of the present invention relates to a method for suppression of microglia activation induced by amyloid β peptide in vivo or in vitro comprising:

administrating the turmeric extract or at least one of termeronol A and termeronol B to microglia in vivo or in vitro; and suppressing activation of the microglia induced by amyloid β peptide.

The microglia in the method according to the present aspect is derived typically from a human. The microglia may also be derived from non-human mammals, such as rat, mouse, or cow.

Microglia may be cells having functions equivalent to those of microglia, such as macrophage cells differentiated from monocytes.

In the method according to the present aspect, a method of administration of the turmeric extract or at least one of termeronol A and termeronol B to microglia in vitro comprises adding the turmeric extract or at least one of termeronol A and termeronol B at adequate concentration to a medium in which the microglia are cultured. The concentration of the turmeric extract or at least one of termeronol A and termeronol B to be added to the medium is not particularly limited. When the turmeric extract is administered, the concentration is preferably 10 µg/ml or higher, more preferably 20 µg/ml or higher, and particularly preferably 50 µg/ml or higher to preferably 1,000 µg/ml or lower, and more preferably 500 µg/ml or lower. When at least one of termeronol A and termeronol B is administered, the concentration of termeronol A and termeronol B in total is preferably 1 µM or higher, more preferably 10 µM or higher, particularly preferably 20 µM or higher, and most preferably 50 µM or higher to preferably 1,000 µM or lower, more preferably 500 µM or lower, and particularly preferably 200 µM or lower.

In the method according to the present aspect, a method of administration of the turmeric extract or at least one of termeronol A and termeronol B to microglia in vivo is not particularly limited, provided that the turmeric extract or at least one of termeronol A and termeronol B can be delivered to microglia in vivo. For example, oral administration, intranasal administration, intracerebral administration, or intraspinal administration is preferable, oral or intranasal administration is more preferable, and oral administration is particularly preferable. When the turmeric extract or at least one of termeronol A and termeronol B is administered to microglia in vivo, the amount of administration is not particularly limited, provided that microglia activation induced by amyloid β peptide can be effectively suppressed. When it is administered to an adult, for example, the amount of the turmeric extract or at least one of termeronol A and termeronol B to be administered to an adult per day is preferably 100 µg or more termeronol A and termeronol B in total, more preferably 80 µg or more termeronol A and/or 20 µg or more termeronol B, and particularly preferably 80 µg or more termeronol A and 20 µg or more termeronol B.

In the method according to the present aspect, the turmeric extract or at least one of termeronol A and termeronol B is administered to microglia in vivo or in vitro, and the turmeric extract or at least one of termeronol A and termeronol B is then kept in contact with the microglia for an adequate period of time, such as 5 hours or longer, preferably 12 hours or longer, more preferably 20 hours or longer, and particularly preferably 24 hours or longer to preferably 72 hours or shorter, more preferably 48 hours or shorter, and particularly preferably 36 hours or shorter. Thus, microglia activation induced by amyloid β peptide can be suppressed.

The amyloid β peptide is typically derived from the same organism species as the microglia.

"Microglia activation induced by amyloid β peptide" is, for example, production of at least one substance selected from among PGE2, TNF-α, and IL-1β by microglia induced by amyloid β peptide. In the present aspect, production of such substances can be suppressed.

<Method for Suppression of Production of at Least One Substance Selected from Among PGE2, TNF-α, and IL-1β Induced by Amyloid β Peptide>

A further aspect of the present invention relates to a method for suppressing production of at least one substance selected from PGE2, TNF-α, and IL-1β induced by amyloid β peptide comprising:

administrating the turmeric extract or at least one of termeronol A and termeronol B to a subject in need of suppression of production of at least one substance selected from among PGE2, TNF-α, and IL-1β induced by amyloid β peptide; and suppressing production of at least one substance selected from among PGE2, TNF-α, and IL-1β induced by amyloid β peptide in the subject.

The turmeric extract or at least one of termeronol A and termeronol B used in the method according to the present aspect can be in the form of the composition of the present invention described above.

The subject in the method according to the present aspect is typically a human. The subject may also be non-human mammals.

In the method according to the present aspect, a route of administration is preferably oral administration, intranasal administration, intracerebral administration, or intraspinal administration, more preferably oral or intranasal administration, and particularly preferably oral administration.

In the method according to the present aspect, the amount of the turmeric extract or at least one of termeronol A and termeronol B to be administered to the subject is not particularly limited, provided that it is an effective amount for suppression of production of at least one substance selected from among PGE2, TNF-α, and IL-1β induced by amyloid peptide. When the subject is an adult, for example, the amount of the turmeric extract or at least one of termeronol A and termeronol B to be administered to an adult per day is preferably 100 µg or more termeronol A and termeronol B in total, more preferably 80 µg or more termeronol A and/or 20 µg or more termeronol B, and particularly preferably 80 µg or more termeronol A and 20 µg or more termeronol B.

EXAMPLES

1. Experiment 1

1.1. Method for Production of Turmeric Extract

A turmeric extract was prepared by extracting the rhizome part of turmeric (*Curcuma longa*) with water, and heat-drying the extract under a reduced pressure to remove water. The amounts of termeronol A and termeronol B in the turmeric extract were measured via LC/MS in accordance with the procedure described below. The measured amount of termeronol A in the turmeric extract was 189 µg/g, and that of termeronol B was 24 µg/g.

1.2. Analysis of Termeronol a and Termeronol B

The turmeric extract was weighed, water and ethyl acetate were added, the resultant was centrifuged, the resulting supernatant was allowed to pass through the active carbon column, the resultant was concentrated with nitrogen gas, and the concentrate was dissolved in acetonitrile. The resulting solution was subjected to LC/MS analysis as a sample. The LC/MS analysis was performed under the conditions described below.

Analysis apparatus: Orbitrap LCMS (Orbitrap Velos Pro), Thermo Fisher Scientific
Flow rate: 0.5 ml/min
Mobile phase: acetonitriole with 0.1% formic acid
Liquid phase gradient:

TABLE 1

| Acetonitrile concentration | Duration |
|---|---|
| 35% → 65% | 20 min |
| 65% | 10 min |
| 65% → 95% | 5 min |
| 95% | 10 min |
| 95% → 35% | 1 min |
| 35% | 9 min |

Column used: UNISON UK-C18 (250 mm×4.6 mm, 3 µm)
Column temperature: 30° C.

1.3. Acquisition of Termeronol a and Termeronol B

Commercial products of termeronol A and termeronol B purchased from Nagara Science Co., Ltd. were dissolved in dimethyl sulfoxide and subjected to the test.

1.4. Evaluation of Activity of Suppressing Activation of Macrophage Cells Induced by Amyloid β Peptide Cells of the human monocytic cell line THP-1 were suspended in RPMI1640 (10% FBS) medium, the cells were seeded in a 96-well plate at $8.0 \times 10^4$ cells/well, 100 nM 12-O-tetradecanoylphorbol 13-acetate (PMA, differentiation-inducing factor) was added thereto, and culture was conducted in the presence of 5% $CO_2$ for 24 hours to differentiate the cells into macrophage cells. Thereafter, the medium was exchanged with another RPMI1640 (10% FBS) medium containing either the turmeric extracts (50, 100, and 200 µg/ml), termeronol A (12.5, 25, 50, or 100 µM), or termeronol B (12.5, 25, 50, or 100 µM), and culture was conducted in the presence of 5% $CO_2$ for 24 hours to treat the cells with each specimen. Thereafter, the medium was exchanged with another RPMI1640 (2% FBS) medium containing an aggregate of 25 µM amyloid β peptides (Aβ), and culture was conducted in the presence of 5% $CO_2$ for 24 hours to activate the cells. Thereafter, prostaglandin E2 (PGE2), the tumor necrosis factor α (TNF-α), and interleukin-1β (IL-1β) released in the medium were assayed via ELISA.

Figure 1:
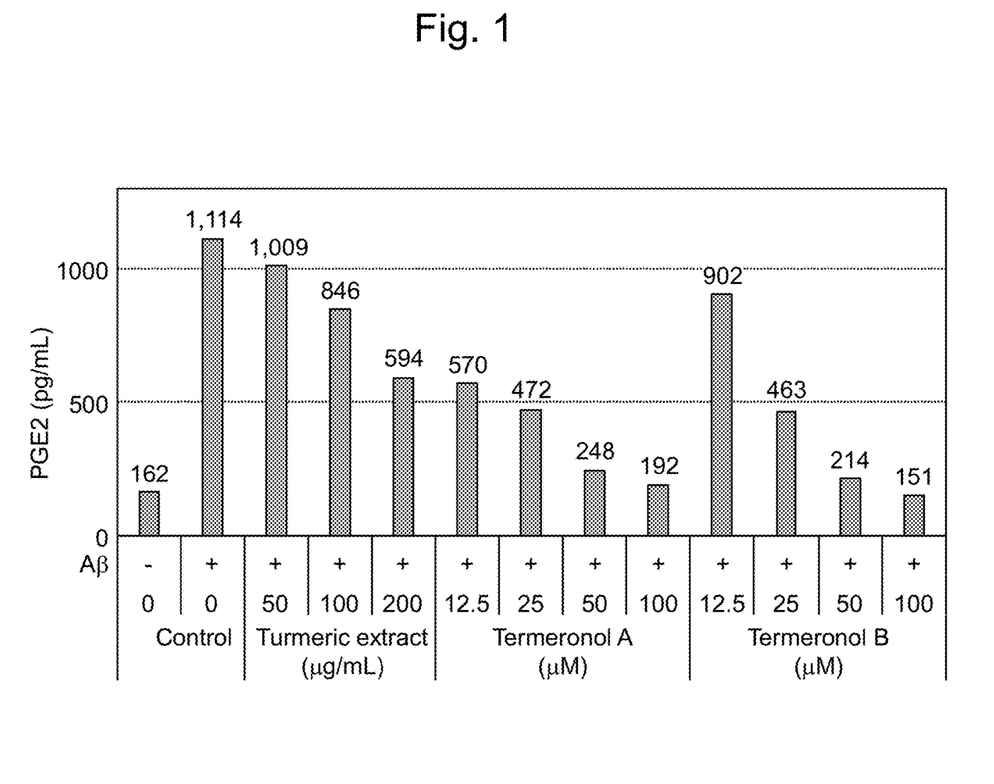
FIG. 1 shows that macrophage cells differentiated from THP-1 cells are activated by treatment of an aggregate of amyloid β peptides, PEG2 production is enhanced, and 50 to 200 µg/ml of a turmeric extract and 12.5 to 100 µM termeronol A and termeronol B suppress the enhancement of PEG2 production.
Figure 2:
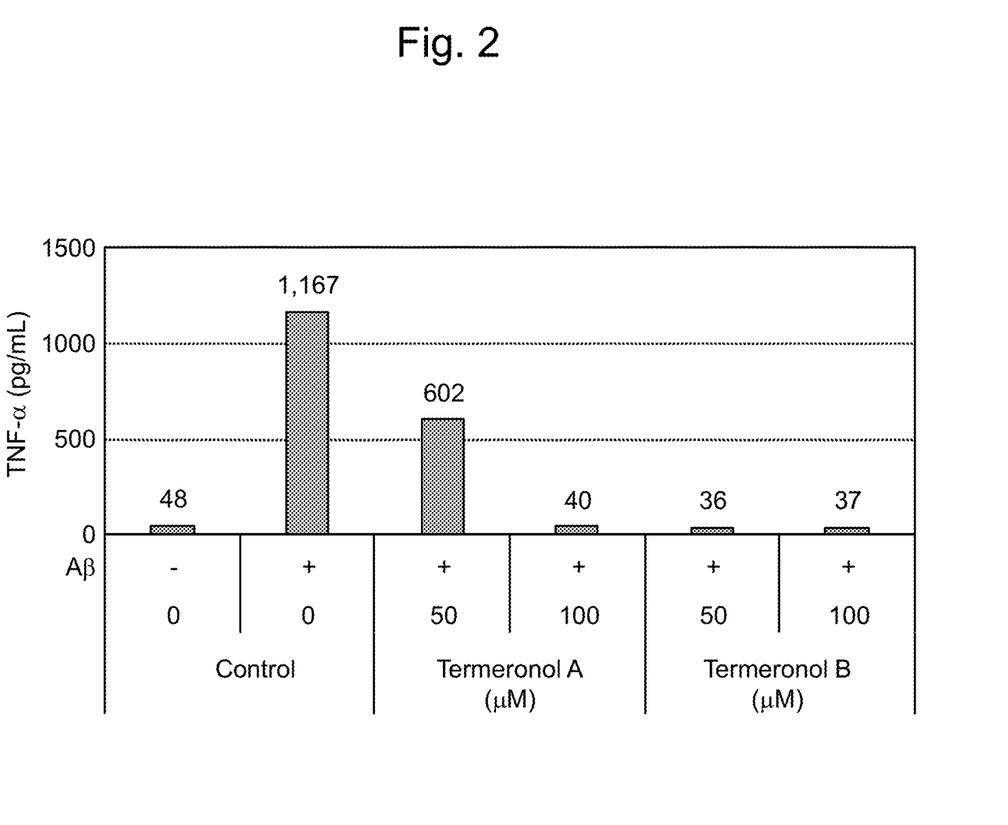
FIG. 2 shows that macrophage cells differentiated from THP-1 cells are activated by treatment of an aggregate of amyloid β peptides, TNF-α production is enhanced, and 50 µM and 100 µM termeronol A and termeronol B suppress the enhancement of TNF-α production.
Figure 3:
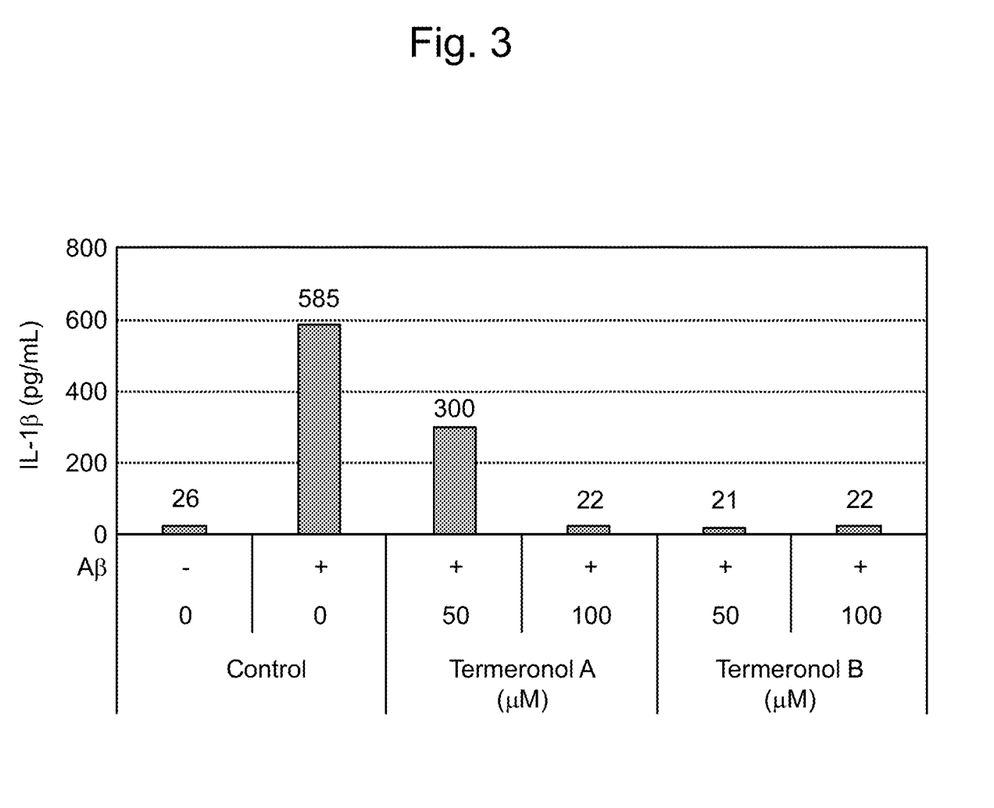
FIG. 3 shows that macrophage cells differentiated from THP-1 cells are activated by treatment of an aggregate of amyloid β peptides, IL-1β production is enhanced, and 50 µM and 100 µM termeronol A and termeronol B suppress the enhancement of IL-1β production.

FIG. 1 shows that macrophage cells differentiated from THP-1 cells are activated by treatment of Aβ, PEG2 production is enhanced, and 50 to 200 µg/ml of the turmeric extract and 12.5 to 100 µM termeronol A and termeronol B suppress the enhancement of PEG2 production. FIG. 2 shows that macrophage cells differentiated from THP-1 cells are activated by treatment of Aβ, TNF-α production is enhanced, and 50 µM and 100 µM termeronol A and termeronol B suppress the enhancement of TNF-α production. FIG. 3 shows that macrophage cells differentiated from THP-1 cells are activated by treatment of Aβ, IL-1β production is enhanced, and 50 µM and 100 µM termeronol A and termeronol B suppress the enhancement of IL-1β production.

Macrophage cells can be regarded as substantially equivalent to microglia based on the markers expressed, and they are used as alternatives to microglia in the in vitro test (e.g., Frontiers in Pharmacology/Neuropharmacology, E. Solito et al, 2012-2, Volume 3, Article 14, International Journal of Alzheimer's Disease, Volume 2012, Article ID 314185, 11 pages). In a patient with Alzheimer's disease, it is deduced that microglia activated by Aβ produce PGE2, TNF-α, and IL-1β and induce cell death of brain nerve cells. Accordingly, the results of the experiment such that the turmeric extract, termeronol A, and termeronol B would suppress production of PGE2, TNF-α, or IL-1β by macrophage cells activated by Aβ verify that the turmeric extract, termeronol A, and termeronol B would suppress production of PGE2, TNF-α, or IL-1β by microglia activated by Aβ and induction of brain nerve cell death in a patient with Alzheimer's disease.

2. Experiment 2

2.1. Method

Cells of the human monocytic cell line THP-1 were suspended in RPMI1640 (10% FBS) medium, the cells were seeded in a 96-well plate at $8.0 \times 10^4$ cells/well, 100 nM 12-O-tetradecanoylphorbol 13-acetate (PMA, differentiation-inducing factor) was added thereto, and culture was conducted in the presence of 5% $CO_2$ for 24 hours to differentiate the cells into macrophage cells. Thereafter, the medium was exchanged with another RPMI1640 (10% FBS) medium containing either the turmeric extract (100 μg/ml) as used in Experiment 1 or termeronol B (50 μM) (Nagara Science Co., Ltd.), and culture was conducted in the presence of 5% $CO_2$ for 24 hours to treat the cells with the turmeric extract (at each concentration) or termeronol B. Thereafter, the medium was exchanged with another RPMI1640 (2% FBS) medium containing an aggregate of 25 μM amyloid β peptides (Aβ), and culture was conducted in the presence of 5% $CO_2$ for 12 hours to activate the macrophage cells. The culture supernatant was collected and designated as a conditioned medium. Separately, human neuroblastoma SHSY5Y cells were suspended in DMEM (10% FBS) medium, seeded in a 96-well plate at $3 \times 10^4$ cells/well, and then cultured in the presence of 5% $CO_2$ for 24 hours. Thereafter, the medium used for human neuroblastoma cell culture was exchanged with the conditioned medium, and culture was conducted in the presence of 5% $CO_2$ for 48 hours to treat the cells in the conditioned medium. Thereafter, cell activity was assayed via WST-1 assays.

WST-1 assays comprise: adding WST-1 (2-(4-iodophenyl)-3-(4-nitrophenyl)-5-(2,4-disulfophenyl)-2H-tetrazolium, monosodium salt, Dojindo Laboratories) to each well containing cells; conducting culture in a $CO_2$ incubator for a given period of time to generate water-soluble formazan from WST-1 with the activity of dehydrogenase in mitochondria of viable cells; and assaying the concentration of the generated formazan. The concentration of the generated formazan is an indicator of cell activity. The formazan concentration was determined based on the absorbance at 450 nm using a microplate reader (reference wavelength: 630 nm).

The procedure of the control test is as described below. The macrophage cells differentiated from THP-1 were cultured in RPMI1640 (10% FBS) free from the turmeric extract or termeronol B in the presence of 5% $CO_2$ for 24 hours, the medium was exchanged with another RPMI1640 (2% FBS) medium containing an aggregate of 25 μM amyloid β peptides (Aβ) (Aβ+) or RPMI1640 (2% FBS) medium free from the aggregate (ADA culture was conducted in the presence of 5% $CO_2$ for 12 hours, and the culture supernatant was collected. The human neuroblastoma cells were treated with the collected culture supernatant instead of the conditioned medium described above.

2.2. Results

Figure 4:
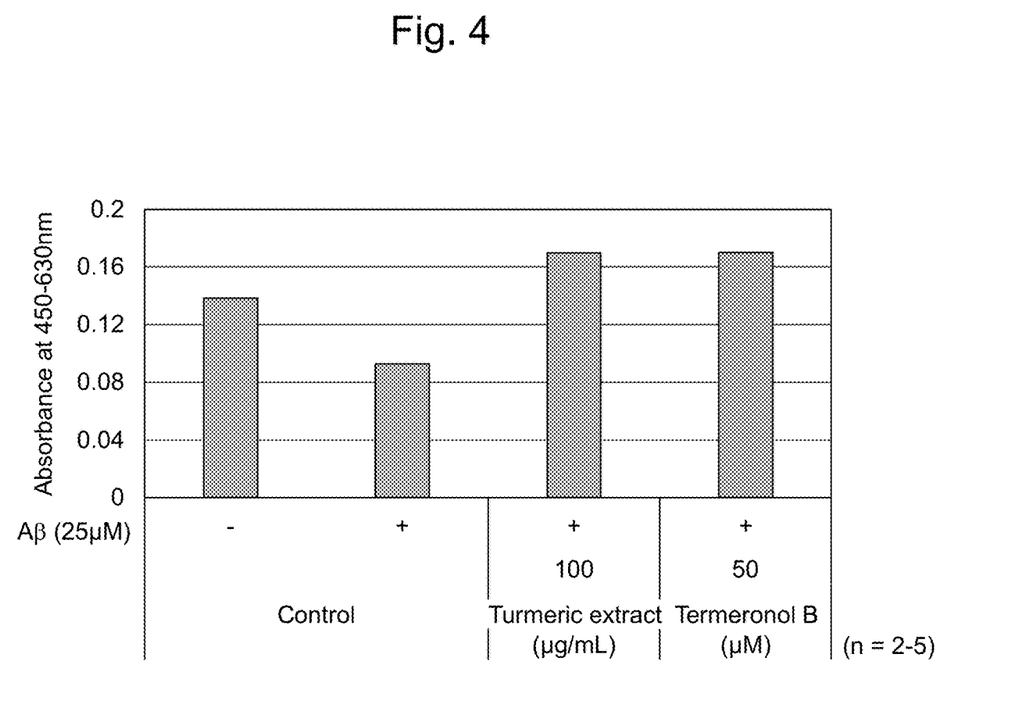
FIG. 4 shows that the culture supernatant of macrophage cells differentiated from THP-1 cells in a medium containing an aggregate of amyloid β peptides induces nerve cell death, while the culture supernatant of macrophage cells treated with a water extract of turmeric or termeronol B in advance suppresses the activity of inducing cell death of human neuroblastoma SHSY5Y cells in a medium containing an aggregate of amyloid β peptides.

The results are shown in FIG. 4. The vertical axis indicates the absorbance measured in the assays, which is cell activity.

In the control test (Aβ+), amyloid β peptide was added to the macrophage cells, culture of the macrophage cells was conducted for a given period of time, and the culture supernatant was collected and added to SHSY5Y. As a result, cell death was induced. In contrast, cell death was not induced in the control test that did not involve the use of amyloid β peptide (Aβ-). On the basis thereof, it was deduced that macrophage cells cultured in a medium supplemented with amyloid β peptide released humoral factors in the culture supernatant and that the humoral factors induced cell death of brain neuronal cells.

When the macrophage cells treated with the turmeric extract or termeronol B in advance were cultured in the presence of amyloid β peptide, in contrast, activity of the culture supernatant for inducing cell death of brain neuronal cells was more suppressed, compared with the control test (Aβ+). This indicates that the turmeric extract and termeronol B suppress the humoral factors released by the macrophage cells in the presence of amyloid β peptide.

3. Experiment 3

3.1. Method

It is known that cell death is induced by oxidative stress resulting from treatment of brain neuronal cells with hydrogen peroxide ($H_2O_2$). In the experiment below, activity of the turmeric extract prepared in Experiment 1 to suppress brain neuronal cell death induced by oxidative stress.

Human neuroblastoma SHSY5Y cells were suspended in DMEM (10% FBS) medium, seeded in a 96-well plate at $3 \times 10^4$ cells/well, and then cultured in the presence of 5% $CO_2$ for 24 hours. Thereafter, the medium was exchanged with DMEM (FBS free) medium containing the turmeric extract described in Experiment 1 (25, 50, 100, or 200 μg/ml), and culture was conducted in the presence of 5% $CO_2$ for 24 hours to treat the cells with the turmeric extract of each concentration. Thereafter, the medium was exchanged with DMEM (FBS free) medium containing 60 μM $H_2O_2$, and culture was conducted in the presence of 5% $CO_2$ for 24 hours to stimulate the cells. Thereafter, cell activity was assayed via WST-1 assays in the same manner as in Experiment 2.

The control test ($H_2O_2$+) was performed in the same manner as in the control test above, except that a DMEM medium containing no turmeric extract (FBS free) was used instead of the DMEM (FBS free) medium containing a turmeric extract at a given concentration. The control test ($H_2O_2$—) was performed in the same manner as described above, except that a DMEM (FBS free) medium containing no turmeric extract was used instead of the DMEM (FBS free) medium containing a turmeric extract at a given concentration and a DMEM (FBS free) medium containing no $H_2O_2$ was used instead of the DMEM (FBS free) medium containing 60 μM $H_2O_2$ above.

3.2. Results

Figure 5:
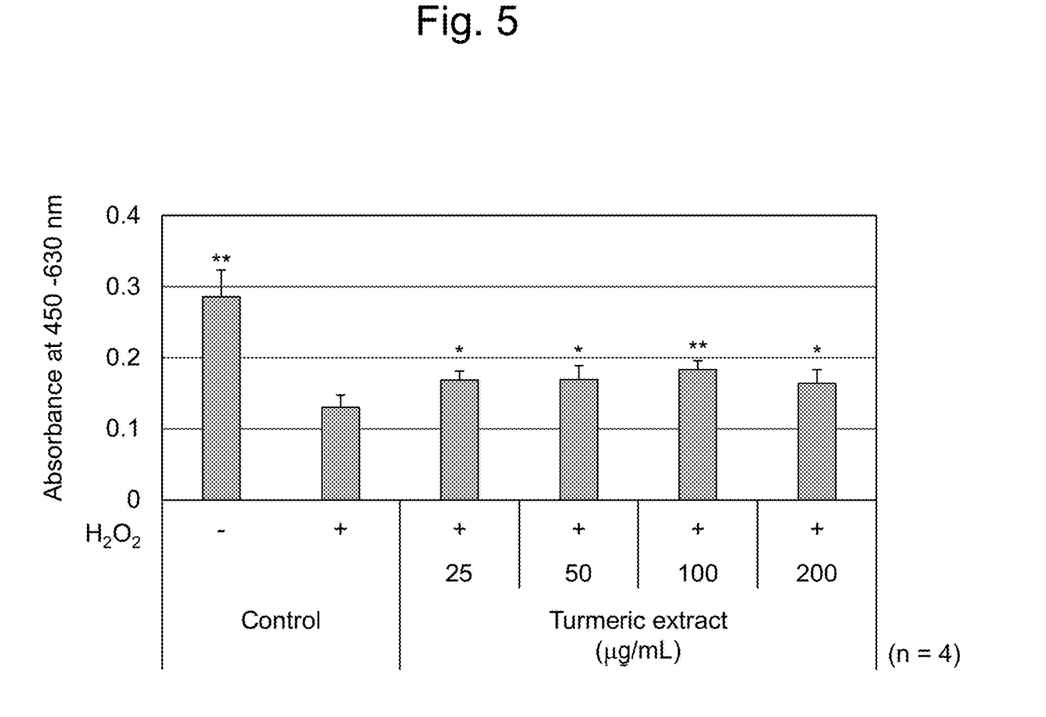
FIG. 5 shows that cell death of the human neuroblastoma SHSY5Y cells induced by oxidative stress is suppressed by a water extract of turmeric.

The results are shown in FIG. 5. The vertical axis indicates the absorbance measured in the assays, which is cell activity. An error bar indicates a standard deviation.

The Student's T test was performed to examine a significant difference between each condition and the control ($H_2O_2$+) (**: $p<0.01$; *: $p<0.05$).

The results shows that cell death of the human neuroblastoma SHSY5Y cells induced by oxidative stress is suppressed by the turmeric extract prepared in Experiment 1.

All publications, patents, and patent applications cited herein are incorporated herein by reference in their entirety.

The invention claimed is:

1. A method for suppression of microglia activation induced by amyloid β peptide in vivo or in vitro comprising:
   administering turmeronol A and turmeronol B to microglia in vivo or in vitro; and
   suppressing microglia activation induced by amyloid β peptide,
   wherein turmeronol A is administered in an amount of 80 μg or more per day and turmeronol B is administered in an amount of 20 μg or more per day.

2. The method according to claim 1, wherein the microglia activation induced by amyloid β peptide encompasses production of at least one substance selected from the group consisting of PGE2, TNF-α, and IL-1β by the microglia induced by amyloid β peptide.

3. The method according to claim 1, wherein at least one of turmeronol A and turmeronol B is in the form of a turmeric extract extracted with at least one extraction solvent selected from the group consisting of water and a hydrophilic organic solvent.

4. The method according to claim 3, wherein the extraction solvent comprises water.

5. The method according to claim 4, wherein the water has a temperature of 95° C. or higher.

6. The method according to claim 3, wherein the extraction solvent comprises an alcohol.

7. The method according to claim 3, wherein the extraction solvent comprises ethanol.

8. The method according to claim 3, wherein the extraction solvent comprises water and an alcohol.

9. The method according to claim 8, wherein the water and the alcohol are mixed at a ratio of 10:90 to 90:10.

10. The method according to claim 8, wherein the water and the alcohol are mixed at a ratio of 20:80 to 50:50.

11. The method according to claim 3, wherein the extraction solvent comprises supercritical carbon dioxide.

12. The method according to claim 1, wherein turmeronol A and turmeronol B are extracted from *Curcuma longa*.

13. The method according to claim 1, wherein the administering is achieved orally, intranasally, intracerebrally, or intraspinally.

14. The method according to claim 1, wherein the administering is achieved orally or intranasally.

15. The method according to claim 1, wherein turmeronol A and turmeronol B are administered as a composition further comprising a sweetener, an acidulant, a vitamin, a mineral, a thickener, an emulsifier, an antioxidant, or water.

16. A method for treatment, prevention, or amelioration of Alzheimer's disease comprising suppressing microglia activation induced by amyloid β peptide according to the method of claim 1.

17. The method according to claim 16, wherein at least one of turmeronol A and turmeronol B is in the form of a turmeric extract extracted with at least one extraction solvent selected from water and a hydrophilic organic solvent.

18. A method for suppression of brain neuronal cell death in vivo or in vitro comprising suppressing microglia activation induced by amyloid β peptide according to the method of claim 1.

19. The method according to claim 18, wherein at least one of turmeronol A and turmeronol B is in the form of a turmeric extract extracted with at least one extraction solvent selected from water and a hydrophilic organic solvent.

* * * * *